US006528039B2

(12) United States Patent
Unger

(10) Patent No.: US 6,528,039 B2
(45) Date of Patent: *Mar. 4, 2003

(54) LOW DENSITY MICROSPHERES AND THEIR USE AS CONTRAST AGENTS FOR COMPUTED TOMOGRAPHY AND IN OTHER APPLICATIONS

(75) Inventor: Evan C. Unger, Tucson, AZ (US)

(73) Assignee: Bristol-Myers Squibb Medical Imaging, Inc., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/878,233

(22) Filed: Jun. 18, 1997

(65) Prior Publication Data

US 2001/0024639 A1 Sep. 27, 2001

Related U.S. Application Data

(60) Continuation of application No. 08/594,269, filed on Jan. 30, 1996, now abandoned, which is a division of application No. 08/456,738, filed on Jun. 1, 1995, now Pat. No. 5,527,521, which is a division of application No. 08/449,090, filed on May 24, 1995, now Pat. No. 5,547,656, which is a division of application No. 08/116,982, filed on Sep. 7, 1993, now Pat. No. 5,456,900, which is a division of application No. 07/980,594, filed on Jan. 19, 1993, now Pat. No. 5,281,408, which is a division of application No. 07/680,984, filed on Apr. 5, 1991, now Pat. No. 5,205,290.

(51) Int. Cl.$^7$ .......................... A61K 49/00; B01F 17/00
(52) U.S. Cl. ............................ 424/9.4; 516/11; 516/77
(58) Field of Search ............................. 424/9.52, 9.4, 424/450, 489; 516/11, 77

(56) References Cited

U.S. PATENT DOCUMENTS

| | | | |
|---|---|---|---|
| 3,015,128 A | 1/1962 | Sommerville et al. | 18/2.6 |
| 4,533,254 A | 8/1965 | Cook et al. | 366/176 |
| 3,291,843 A | 12/1966 | Fritz et al. | 260/614 |
| 3,293,114 A | 12/1966 | Kenaga et al. | 162/168 |
| 3,479,811 A | 11/1969 | Walters | 57/153 |
| 3,488,714 A | 1/1970 | Walters et al. | 161/161 |
| 3,535,500 A | 10/1970 | Priest et al. | 96/91 |
| 3,557,294 A | 1/1971 | Dear et al. | 424/342 |
| 3,594,326 A | 7/1971 | Himmel et al. | 252/316 |
| 3,615,972 A | 10/1971 | Morehouse et al. | 156/79 |
| 3,650,831 A | 3/1972 | Jungermann et al. | 134/27 |
| 3,732,172 A | 5/1973 | Herbig et al. | 252/316 |
| 3,873,564 A | 3/1975 | Schneider et al. | 270/309.6 |
| 3,945,956 A | 3/1976 | Garner | 260/2.5 B |
| 3,960,583 A | 6/1976 | Netting et al. | 106/122 |
| 3,968,203 A | 7/1976 | Spitzer et al. | 424/47 |
| 4,027,007 A | 5/1977 | Messina | 424/46 |
| 4,089,801 A * | 5/1978 | Schneider | 252/316 |
| 4,108,806 A | 8/1978 | Cohrs et al. | 521/54 |
| 4,138,383 A | 2/1979 | Rembaum et al. | 260/29.7 H |
| 4,162,282 A | 7/1979 | Fulwyler et al. | 274/9 |
| 4,179,546 A | 12/1979 | Garner et al. | 521/56 |
| 4,192,859 A | 3/1980 | Mackaness et al. | 424/5 |
| 4,224,179 A | 9/1980 | Schneider | 252/316 |
| 4,229,360 A * | 10/1980 | Schneider et al. | 270/403 |
| 4,265,251 A | 5/1981 | Tickner | 128/660 |
| 4,276,885 A | 7/1981 | Tickner et al. | 128/660 |
| 4,310,505 A | 1/1982 | Baldeschwieler et al. | 424/1 |
| 4,310,506 A | 1/1982 | Baldeschwieler et al. | 424/1 |
| 4,315,514 A | 2/1982 | Drewes et al. | 128/653 |
| 4,331,654 A | 5/1982 | Morris | 424/38 |
| 4,334,929 A | 8/1982 | Bonsen et al. | 424/15 |
| 4,342,826 A | 8/1982 | Cole | 435/7 |
| 4,420,442 A | 12/1983 | Sands | 264/13 |
| 4,421,562 A | 12/1983 | Sands et al. | 106/75 |
| 4,426,330 A * | 1/1984 | Sears | 270/403 |
| 4,427,649 A | 1/1984 | Dingle et al. | 424/38 |
| 4,428,924 A | 1/1984 | Millington | 424/4 |
| 4,442,843 A | 4/1984 | Rasor et al. | 128/660 |

(List continued on next page.)

FOREIGN PATENT DOCUMENTS

| | | |
|---|---|---|
| AU | AU-B-30351/89 | 3/1983 |
| AU | AU 641363 | 3/1990 |
| AU | 641363 | 3/1990 |
| AU | B-30351-89 | 3/1993 |
| DE | 25 21 003 | 8/1976 |
| DE | 38 03 972 A1 | 8/1989 |
| EP | 0 052 575 | 5/1982 |

(List continued on next page.)

OTHER PUBLICATIONS

Frézard, F., et al., "Fluorinated phosphatidylcholine–based liposomes: H+/NA+ permeability, active doxorubicin encapsulation and stability in human serum," *Biochimica et Biophysica Acta 1194*, 1994, XP–000990899, 61–68.

Gross, U., et al., "Phospholipid vesiculated fluorocarbon—promising trend in blood substitutes," *Biomat., Art. Cells & Immob. Biotech.*, 1992, XP–000990913, 20(2–4), 831–833.

Riess, J.G., "Du fluor dans nos artères (!)," *New J. Chem.,*, 1995, XP–000990897, 19, 891–909 (English Language Abstract).

(List continued on next page.)

*Primary Examiner*—Michael G. Hartley
(74) *Attorney, Agent, or Firm*—Woodcock Washburn LLP

(57) ABSTRACT

Substantially homogeneous aqueous suspensions of low density microspheres are presented as contrast media for imaging the gastrointestinal tract and other body cavities using computed tomography. In one embodiment, the low density microspheres are gas-filled. With computed tomography, the contrast media serve to change the relative density of certain areas within the gastrointestinal tract and other body cavities, and improve the overall diagnostic efficacy of this imaging method.

16 Claims, No Drawings

U.S. PATENT DOCUMENTS

| | | | | |
|---|---|---|---|---|
| 4,466,442 A | 8/1984 | Hilmann et al. | ............ | 128/653 |
| 4,485,193 A | 11/1984 | Rubens et al. | ................ | 521/58 |
| 4,530,360 A | 7/1985 | Duarte | ................... | 128/419 F |
| 4,534,899 A | * 8/1985 | Sears | ........................ | 270/403 |
| 4,540,629 A | 9/1985 | Sands et al. | ................. | 428/402 |
| 4,544,545 A | 10/1985 | Ryan et al. | ................... | 424/1.1 |
| 4,549,892 A | 10/1985 | Baker et al. | ................. | 65/21.4 |
| 4,569,836 A | 2/1986 | Gordon | ........................ | 424/1.1 |
| 4,572,203 A | 2/1986 | Feinstein | .................... | 128/653 |
| 4,586,512 A | 5/1986 | Do-huu et al. | .............. | 128/660 |
| 4,603,044 A | 7/1986 | Geho et al. | ....................... | 424/9 |
| 4,615,879 A | 10/1986 | Runge et al. | ................... | 424/9 |
| 4,620,546 A | 11/1986 | Aida et al. | ................... | 128/660 |
| 4,621,023 A | 11/1986 | Redziniak et al. | ........ | 428/402.2 |
| 4,646,756 A | 3/1987 | Watmough et al. | .......... | 128/804 |
| 4,657,756 A | 4/1987 | Rasor et al. | .................... | 424/9 |
| 4,658,828 A | 4/1987 | Dory | ........................ | 128/660 |
| 4,663,161 A | 5/1987 | Mannino et al. | ............... | 424/89 |
| 4,675,310 A | 6/1987 | Chapman et al. | .............. | 514/6 |
| 4,681,119 A | 7/1987 | Rasor et al. | ................. | 128/660 |
| 4,684,479 A | 8/1987 | D'Arrigo | .................... | 252/307 |
| 4,689,986 A | 9/1987 | Carson et al. | ................... | 73/19 |
| 4,693,999 A | 9/1987 | Axelsson et al. | ............ | 514/174 |
| 4,718,433 A | 1/1988 | Feinstein et al. | ........... | 128/660 |
| 4,728,575 A | 3/1988 | Gamble al. | .............. | 428/402.2 |
| 4,728,578 A | 3/1988 | Higgins et al. | .............. | 428/462 |
| 4,731,239 A | 3/1988 | Gordon | ........................ | 424/9 |
| 4,737,323 A | 4/1988 | Martin et al. | ................. | 274/4.3 |
| 4,767,610 A | 8/1988 | Long | .............................. | 424/5 |
| 4,774,958 A | 10/1988 | Feinstein | ............... | 128/660.01 |
| 4,775,522 A | 10/1988 | Clark, Jr. | ........................ | 424/9 |
| 4,776,991 A | 10/1988 | Farmer et al. | ................ | 274/4.3 |
| 4,781,871 A | 11/1988 | West III et al. | .............. | 274/4.3 |
| 4,789,501 A | 12/1988 | Day et al. | .................... | 252/645 |
| 4,790,891 A | 12/1988 | Halliday et al. | ............... | 149/2 |
| 4,822,534 A | 4/1989 | Lencki et al. | ................ | 264/4.3 |
| 4,830,828 A | 5/1989 | Payne et al. | ................ | 424/450 |
| 4,834,964 A | 5/1989 | Rosen | ........................... | 424/9 |
| 4,844,882 A | 7/1989 | Widder et al. | .................. | 424/9 |
| 4,863,717 A | 9/1989 | Keana | ........................... | 424/9 |
| 4,865,836 A | 9/1989 | Long, Jr. | ....................... | 424/5 |
| 7,866,096 | 9/1989 | Schweighardt | ............... | 514/756 |
| 4,877,561 A | 10/1989 | Iga et al. | ..................... | 274/4.3 |
| 4,893,624 A | 1/1990 | Lele | ........................... | 128/399 |
| 4,895,719 A | 1/1990 | Radhakrishnan | ............. | 424/45 |
| 4,895,876 A | 1/1990 | Schweighardt, et al. | ...... | 514/747 |
| 4,898,734 A | 2/1990 | Mathiowitz et al. | ......... | 424/426 |
| 4,900,540 A | 2/1990 | Ryan et al. | ..................... | 424/9 |
| 4,918,065 A | 4/1990 | Stindl et al. | ................. | 514/179 |
| 4,919,895 A | 4/1990 | Heldebrant et al. | ......... | 422/129 |
| 4,921,706 A | 5/1990 | Roberts et al. | ................ | 424/450 |
| 4,927,623 A | 5/1990 | Long, Jr. | ....................... | 424/5 |
| 4,933,121 A | 6/1990 | Law et al. | .................... | 264/4.3 |
| 4,938,947 A | 7/1990 | Nicolau et al. | ............... | 424/1.1 |
| 4,957,656 A | 9/1990 | Cerny et al. | ................. | 252/311 |
| 4,972,002 A | 11/1990 | Volkert | ..................... | 521/120 |
| 4,981,692 A | 1/1991 | Popescu et al. | ............. | 424/422 |
| 4,984,573 A | 1/1991 | Leunbach | ................... | 128/653 |
| 4,985,550 A | 1/1991 | Charpiot et al. | ........... | 536/18.4 |
| 4,987,754 A | * 1/1991 | Long, Jr. | .................... | 514/772 |
| 4,993,415 A | 2/1991 | Long | ........................ | 128/653 A |
| 4,996,041 A | 2/1991 | Arai et al. | ..................... | 424/9 |
| 5,000,960 A | 3/1991 | Wallach | ..................... | 424/450 |
| 5,004,611 A | 4/1991 | Leigh | ........................ | 424/450 |
| 5,008,050 A | 4/1991 | Cullis et al. | ................. | 274/4.3 |
| 5,008,109 A | 4/1991 | Tin | ........................... | 424/422 |
| 5,013,556 A | 5/1991 | Woodle et al. | ............... | 424/450 |
| 5,019,370 A | 5/1991 | Jay et al. | ..................... | 424/4 |
| 5,045,304 A | 9/1991 | Schneider et al. | ............. | 424/9 |
| 5,049,388 A | 9/1991 | Knight et al. | ............... | 424/450 |
| 4,229,360 A | * 11/1991 | Schneider et al. | .......... | 270/403 |
| 5,077,036 A | 12/1991 | Long, Jr. | ....................... | 424/5 |
| 5,078,994 A | 1/1992 | Nair et al. | ................... | 424/501 |
| 5,080,885 A | 1/1992 | Long, Jr. | ....................... | 424/5 |
| 5,088,499 A | 2/1992 | Unger | ................... | 128/662.02 |
| 5,107,842 A | 4/1992 | Levene et al. | .......... | 128/662.02 |
| 5,114,703 A | 5/1992 | Wolf et al. | ..................... | 424/5 |
| 5,123,414 A | 6/1992 | Unger | ........................ | 128/654 |
| 5,135,000 A | 8/1992 | Akselrod et al. | ....... | 128/662.02 |
| 5,137,928 A | 8/1992 | Erbel et al. | .................... | 521/56 |
| 5,141,738 A | 8/1992 | Rasor et al. | .................... | 424/2 |
| 5,147,631 A | 9/1992 | Glajch et al. | .................... | 424/9 |
| 5,149,319 A | 9/1992 | Under | ........................ | 604/22 |
| 5,171,755 A | 12/1992 | Kaufman | .................... | 514/759 |
| 5,186,922 A | 2/1993 | Shell et al. | ................... | 128/654 |
| 5,190,766 A | 3/1993 | Ishihara | ..................... | 424/489 |
| 5,190,982 A | 3/1993 | Erbel et al. | .................... | 521/56 |
| 5,192,549 A | 3/1993 | Barenolz et al. | ............. | 424/450 |
| 5,193,183 A | 3/1993 | Yudelson et al. | ............... | 424/9 |
| 5,194,188 A | 3/1993 | Guitierrez | .................... | 264/4.1 |
| 5,194,266 A | 3/1993 | Abra et al. | ................... | 424/450 |
| 5,195,520 A | 3/1993 | Schlief et al. | .......... | 128/660.02 |
| 5,196,348 A | 3/1993 | Schweighardt et al. | ...... | 436/173 |
| 5,198,225 A | 3/1993 | Meybeck et al. | ............ | 424/450 |
| 5,205,287 A | 4/1993 | Erbel et al. | ................. | 128/632 |
| 5,205,290 A | 4/1993 | Unger | ..................... | 128/653.4 |
| 5,209,720 A | 5/1993 | Unger | ........................... | 604/22 |
| 5,213,804 A | 5/1993 | Martin et al. | ................ | 424/450 |
| 5,215,680 A | 6/1993 | D'Arrigo | .................... | 252/307 |
| 5,219,538 A | 6/1993 | Henderson et al. | ....... | 428/402.2 |
| 5,228,446 A | 7/1993 | Unger et al. | .......... | 128/662.02 |
| 5,230,882 A | 7/1993 | Unger | ............................ | 424/9 |
| 5,247,935 A | 9/1993 | Cline et al. | ............... | 128/653.2 |
| 5,271,928 A | * 12/1993 | Schneider et al. | .............. | 424/9 |
| 5,281,408 A | 1/1994 | Unger | .......................... | 424/4 |
| 5,283,255 A | 2/1994 | Levy et al. | .................. | 514/410 |
| 5,305,757 A | 4/1994 | Unger et al. | .......... | 128/662.02 |
| 5,310,540 A | 5/1994 | Giddey et al. | .................. | 424/9 |
| 5,315,997 A | 5/1994 | Widder et al. | ............ | 128/653.3 |
| 5,315,998 A | 5/1994 | Tachibana et al. | ...... | 128/660.01 |
| 5,316,771 A | * 5/1994 | Barenholz et al. | ........... | 424/450 |
| 5,334,381 A | 8/1994 | Unger | ........................... | 424/9 |
| 5,339,814 A | 8/1994 | Lasker | ................... | 128/653.4 |
| 5,344,930 A | 9/1994 | Riess et al. | .................... | 544/84 |
| 5,350,571 A | 9/1994 | Kaufman et al. | ................ | 424/9 |
| 5,352,435 A | 10/1994 | Unger | ............................ | 424/9 |
| 5,354,549 A | 10/1994 | Klaveness et al. | .............. | 424/3 |
| 5,358,702 A | 10/1994 | Unger | ............................ | 424/9 |
| 5,362,477 A | 11/1994 | Moore et al. | .................... | 424/9 |
| 5,362,478 A | 11/1994 | Desai et al. | ..................... | 424/9 |
| 5,380,411 A | 1/1995 | Schlief | ...................... | 204/157.15 |
| 5,380,519 A | 1/1995 | Schneider et al. | .............. | 424/9 |
| 5,393,513 A | 2/1995 | Long, Jr. | ....................... | 424/5 |
| 5,393,524 A | 2/1995 | Quay | ............................ | 424/9 |
| 5,403,575 A | 4/1995 | Kaufman, et al. | .............. | 424/5 |
| 5,409,688 A | 4/1995 | Quay | ............................ | 424/9 |
| 5,410,516 A | 4/1995 | Uhlendorf et al. | ............... | 367/7 |
| 5,413,774 A | 5/1995 | Schneider et al. | ........... | 424/9.51 |
| 5,425,366 A | 6/1995 | Reinhardt et al. | ....... | 128/662.02 |
| 5,433,204 A | 7/1995 | Olson | .................... | 128/661.08 |
| 5,445,813 A | 8/1995 | Schneider et al. | .......... | 424/9.51 |
| 5,456,900 A | 10/1995 | Unger | ........................ | 424/9.4 |
| 5,460,800 A | 10/1995 | Walters | ........................ | 429/9.6 |
| 5,469,854 A | 11/1995 | Unger | .................... | 128/662.02 |
| 5,470,582 A | 11/1995 | Supersaxo et al. | ............ | 424/489 |
| 5,485,839 A | 1/1996 | Aida et al. | ................. | 128/653.1 |
| 5,487,390 A | 1/1996 | Cohen et al. | .......... | 128/662.02 |
| 5,496,535 A | 3/1996 | Kirkland | .................... | 424/9.37 |
| 5,496,536 A | 3/1996 | Wolf | ........................ | 424/9.322 |
| 5,498,421 A | 3/1996 | Grinstaff et al. | ............. | 424/450 |
| 5,501,863 A | 3/1996 | Rössling et al. | ............. | 424/489 |

| Patent Number | Date | Inventor | Class |
|---|---|---|---|
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,512,268 A | 4/1996 | Grinstaff et al. | 424/9.322 |
| 5,514,720 A | 5/1996 | Clark, Jr., et al. | 514/749 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A | 7/1996 | Lohrmann et al. | 429/9.52 |
| 5,536,490 A | 7/1996 | Klaveness et al. | 424/9.52 |
| 5,536,753 A | 7/1996 | Clark, Jr. | 514/749 |
| 5,539,814 A | 7/1996 | Shoji | 379/215 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |
| 5,562,893 A | 10/1996 | Lohrmann | 424/9.52 |
| 5,565,215 A | 10/1996 | Gref et al. | 424/501 |
| 5,567,413 A | 10/1996 | Klaveness et al. | 424/9.51 |
| 5,567,414 A | 10/1996 | Schneider et al. | 424/9.52 |
| 5,567,415 A | 10/1996 | Porter | 424/9.52 |
| 5,567,765 A | 10/1996 | Moore et al. | 524/801 |
| 5,569,448 A | 10/1996 | Wong et al. | 424/9.45 |
| 5,569,449 A | 10/1996 | Klaveness et al. | 424/9.51 |
| 5,571,498 A | 11/1996 | Cacheris, et al. | 424/9.365 |
| 5,571,797 A | 11/1996 | Ohno et al. | 514/44 |
| 5,573,751 A | 11/1996 | Quay | 424/9.52 |
| 5,578,292 A | 11/1996 | Schneider et al. | 424/9.51 |
| 5,585,112 A | 12/1996 | Unger et al. | 424/450 |
| 5,593,680 A | 1/1997 | Bara et al. | 424/401 |
| 5,595,723 A | 1/1997 | Quay | 424/9.5 |
| 5,605,673 A | 2/1997 | Schutt et al. | 424/9.51 |
| 5,606,973 A | 3/1997 | Lambert et al. | 128/662.02 |
| 5,612,057 A | 3/1997 | Lanza et al. | 424/450 |
| 5,612,318 A | 3/1997 | Weichselbaum et al. | 514/44 |
| 5,614,169 A | 3/1997 | Klaveness et al. | 424/9.52 |
| 5,620,689 A | 4/1997 | Allen et al. | 424/178.1 |
| 5,626,833 A | 5/1997 | Schutt et al. | 424/9.52 |
| 5,635,539 A | 6/1997 | Clark, Jr., et al. | 514/759 |
| 5,639,443 A | 6/1997 | Schutt et al. | 424/9.52 |
| 5,639,473 A | 6/1997 | Grinstaff et al. | 424/450 |
| 5,643,553 A | 7/1997 | Schneider et al. | 424/9.52 |
| 5,648,095 A | 7/1997 | Illum et al. | 424/489 |
| 5,648,098 A | 7/1997 | Porter | 424/490 |
| 5,672,585 A | 9/1997 | Pierschbacher et al. | 514/11 |
| 5,676,928 A | 10/1997 | Klaveness et al. | 424/9.32 |
| 5,679,459 A | 10/1997 | Riess et al. | 428/402.2 |
| 5,686,060 A | 11/1997 | Schneider et al. | 424/9.52 |
| 5,686,102 A | 11/1997 | Gross et al. | 424/450 |
| 5,695,460 A | 12/1997 | Siegel et al. | 604/21 |
| 5,701,899 A | 12/1997 | Porter | 428/662.02 |
| 5,707,352 A | 1/1998 | Sekins et al. | 604/56 |
| 5,707,606 A | 1/1998 | Quay | 424/9.52 |
| 5,707,607 A | 1/1998 | Quay | 424/9.52 |
| 5,711,933 A | 1/1998 | Bichon et al. | 424/9.52 |
| 5,716,597 A | 2/1998 | Lohrmann et al. | 424/9.5 |
| 5,732,707 A | 3/1998 | Widder et al. | 128/661.08 |
| 5,733,527 A | 3/1998 | Schutt | 424/9.52 |
| 5,736,121 A | 4/1998 | Unger | 424/9.4 |
| 5,740,807 A | 4/1998 | Porter | 128/662.02 |
| 5,770,222 A | 6/1998 | Unger et al. | 424/450 |
| 5,785,950 A | 7/1998 | Kaufman, et al. | 424/1.89 |
| 5,804,162 A | 9/1998 | Kabalnov et al. | 424/9.51 |
| 5,830,430 A | 11/1998 | Unger et al. | 424/1.21 |
| 5,840,023 A | 11/1998 | Oraevsky et al. | 600/407 |
| 5,846,514 A | 12/1998 | Unger | 424/9.52 |
| 5,849,727 A | 12/1998 | Porter et al. | 514/156 |
| 5,855,865 A | 1/1999 | Lambert et al. | 424/9.52 |
| 5,858,399 A | 1/1999 | Lanza et al. | 424/450 |
| 5,874,062 A | 2/1999 | Unger | 424/9.4 |
| 5,897,851 A | 4/1999 | Quay et al. | 424/9.52 |
| 5,958,371 A | 9/1999 | Lanza, et al. | 424/9.32 |
| 5,976,501 A | 11/1999 | Jablonski | 424/9.52 |
| 5,980,936 A | 11/1999 | Krafft et al. | 424/450 |
| 5,989,520 A | 11/1999 | Lanza et al. | 424/9.32 |
| 5,997,898 A | 12/1999 | Unger | 424/450 |
| 6,056,938 A | 5/2000 | Unger et al. | 424/1.21 |
| 6,068,857 A | 5/2000 | Weitschies et al. | 424/489 |
| 6,159,445 A | 12/2000 | Klaveness et al. | 424/9.6 |
| 6,258,378 B1 | 7/2001 | Schneider, et al. | 424/450 |
| 6,261,537 B1 | 7/2001 | Klaveness et al. | 424/9.52 |
| 6,331,289 B1 | 12/2001 | Klaveness et al. | 424/9.52 |

FOREIGN PATENT DOCUMENTS

| | | |
|---|---|---|
| EP | 0 107 559 | 5/1984 |
| EP | EP 0 077 752 B1 | 3/1986 |
| EP | 0 224 934 A2 | 6/1987 |
| EP | 0 231 091 * | 8/1987 |
| EP | 0 243 947 | 11/1987 |
| EP | 0 272 091 | 6/1988 |
| EP | WOX 85/01161 | 6/1988 |
| EP | 0 324 938 | 1/1989 |
| EP | 0 320 433 A2 | 6/1989 |
| EP | 0 338 971 | 10/1989 |
| EP | EP 357 163 A1 | 3/1990 |
| EP | 0 359 246 A2 | 3/1990 |
| EP | 0 361 894 | 4/1990 |
| EP | 0 216 730 | 1/1991 |
| EP | EP 441 468 A2 | 8/1991 |
| EP | 0 357 164 B1 | 10/1991 |
| EP | 0 458 745 A1 | 11/1991 |
| EP | 0 467 031 A2 | 1/1992 |
| EP | 0 314 764 B1 | 9/1992 |
| EP | WO 92/17213 * | 10/1992 |
| EP | 0 554 213 A1 | 8/1993 |
| EP | 0 586 875 | 3/1994 |
| EP | EP 0 586 875 * | 3/1994 |
| EP | 0 614 656 A1 | 9/1994 |
| EP | 0 633 030 A1 * | 1/1995 |
| EP | EP 0 727 225 A2 | 8/1996 |
| EP | 0 901 793 A1 | 3/1999 |
| FR | 2 700 952 | 8/1994 |
| GB | 1044680 | 10/1966 |
| GB | 2193095 A | 2/1988 |
| JP | 59-67229 | 4/1984 |
| JP | 62 286534 | 12/1987 |
| JP | 63-60943 | 3/1988 |
| JP | SHO 63-60943 | 3/1988 |
| JP | 2-48522 | 2/1990 |
| JP | 2-196730 | 8/1990 |
| WO | WO 80/02365 | 11/1980 |
| WO | WO 82/01642 | 5/1982 |
| WO | WO 85/02772 | 7/1985 |
| WO | WO 86/00238 | 1/1986 |
| WO | WO 86/01103 | 2/1986 |
| WO | WO 89/05040 | 6/1989 |
| WO | WO 89/10118 | 11/1989 |
| WO | WO 90/01952 | 3/1990 |
| WO | WO 90/04384 | 5/1990 |
| WO | WO 90/04943 | 5/1990 |

| | | |
|---|---|---|
| WO | WO 90/14846 | 12/1990 |
| WO | WO 91/00086 | 1/1991 |
| WO | WO 91/03267 | 3/1991 |
| WO | WO 91/09629 | 7/1991 |
| WO | WO 91/12823 | 9/1991 |
| WO | WO 91-15244 | 10/1991 |
| WO | WO 91/15244 | 10/1991 |
| WO | WO 91/18612 | 12/1991 |
| WO | WO 92/05806 | * 4/1992 |
| WO | WO 92/10166 | 6/1992 |
| WO | WO 92/11873 | 7/1992 |
| WO | WO 92/15284 | 9/1992 |
| WO | WO 92/17212 | * 10/1992 |
| WO | WO 92/17213 | 10/1992 |
| WO | WO 92/17436 | 10/1992 |
| WO | WO 92/17514 | 10/1992 |
| WO | WO 92/21382 | 12/1992 |
| WO | WO 92/22247 | 12/1992 |
| WO | WO 92/22249 | 12/1992 |
| WO | WO 92/22298 | 12/1992 |
| WO | WO 93/00933 | 1/1993 |
| WO | WO 93/05819 | 1/1993 |
| WO | WO 93/06869 | 4/1993 |
| WO | WO 93/13809 | 7/1993 |
| WO | WO 93/17718 | 9/1993 |
| WO | WO 93/20802 | 10/1993 |
| WO | WO 94/00110 | 1/1994 |
| WO | WO 94/06477 | 3/1994 |
| WO | WO 94/07539 | 4/1994 |
| WO | WO 94/09829 | 5/1994 |
| WO | WO 84/02909 | 8/1994 |
| WO | WO 94/16739 | 8/1994 |
| WO | WO 94/21301 | 9/1994 |
| WO | WO 94/21302 | 9/1994 |
| WO | WO 94/28780 | 12/1994 |
| WO | WO 94/28873 | 12/1994 |
| WO | WO 95/03835 | 2/1995 |
| WO | WO 95/06518 | 3/1995 |
| WO | WO 95/07072 | 3/1995 |
| WO | WO 95/23615 | 9/1995 |
| WO | WO 95/24184 | 9/1995 |
| WO | WO 95/32005 | 11/1995 |
| WO | WO 95/32006 | 11/1995 |
| WO | WO 96/04018 | 2/1996 |
| WO | WO 96/09793 | 4/1996 |
| WO | WO 96/36286 | 11/1996 |
| WO | WO 96/40281 | 12/1996 |
| WO | WO 96/40285 | 12/1996 |
| WO | WO 98/00172 | 1/1998 |
| WO | WO 98/04292 | 2/1998 |
| WO | WO 98/18501 | 5/1998 |
| WO | WO 99/13919 | 3/1999 |
| WO | WO 99/39738 | 8/1999 |
| WO | WO 00/45856 | 8/2000 |
| WO | WO 01/15742 | 3/2001 |

OTHER PUBLICATIONS

Riess, J.G., "Introducing a new element—fluorine—into the liposomal membrane," *J. Liposome Res.*, 1995, XP 000525914, 5(3), 413–430.

Santaella, C., et al., "Extended in vivo blood circulation time of fluorinated liposomes," *FEBS 13463*, 1993, XP–000990861, 336(3), 481–484.

Trevino, L., et al., "Incorporation of a perfluoroalkylalkane ($R_FR_H$) into the phospholipid bilayer of DMPC liposomes results in greater encapsulation stability,"60 *J. Liposome Res.*, 1994), XP 000457303, 4(2), 1017–1028.

Zarif, L., et al., "Biodistribution and excretion of a mixed fluorocarbon–hydrocarbon "Dowel" emulsion as determined by $^{19}F$ NMR," *Art. Cells, Blood Subs., and Immob. Biotech.*, 1994, XP–000990914, 22(4), 1193–1198.

Porter, T. R., et al., "Thrombolytic Enhancement with Perfluorocarbon–exposed Sonicated Dextrose Albumin Microbubbles", *American Heart Journal*, Nov. 1996, vol. 132, No. 5, pp. 964–968.

Hautanen, A., et al., "Effects of modifications of the RGD sequence and its context on recognition by the fibronectin receptor," *J. Biol. Chem.*, 1989, 264(3), 1437–1442.

Takeuchi, M., et al., "Enhanced visualization of intravascular thrombus with the use of a thrombus targeting ultrasound contrast agent (MRX408): Evidence from in vivo experimental echocardiographic studies," *J. Am. College of Cardiology*, 1998, 81(12), 1 page, Abstract XP–000952675.

Unger, E.C., et al., "In vitrostudies of a new thrombus–specific ultrasound contrast agent," *J. of Cardiology*, 1998, 81(12), 58G–61G, Abstract XP–002087505.

Wu, Y., et al., "Binding and lysing of blood clots using MRX–408," *Investigate Radiology*, 1998, 33(12), 880–885.

Lejbkowicz et al., "The response of normal and malignant cells to ultrasound in vitro." Database *Biosis*, No. 1993:95122245 (abstract only), 1993.

Jackson et al., "Effect of ultrasound therapy on the repair of Achilles tendon injuries in rats." *Medicine and Science In Sports And Exercise*, vol. 23, No. 2, pp. 171–176, 1991.

Maxwell, "Therapeutic Ultrasound: Its Effects on the Cellular and Molecular Mechanisms of Inflammation and Repair." *Physiotherapy*, vol. 78, No. 6, pp. 421–426, Jun. 1992.

Tuncay et al., "Expression of Genes Associated with Tissue Remodeling Upon Ultrasound Perturbation in the Gingival Fibroblast." *Journal of Dental Research*, vol. 75, p. 143, 1996 (abstract only).

Wang et al., "Low Intensity Ultrasound Treatment Increases Strength in a Rat Femoral Fractural Model." *Journal of Orthopaedic Research*, vol. 12, No. 1, pp. 40–47, 1994.

Yang et al., "Exposure to Low–Intensity Ultrasound Increases Aggrecan Gene Expression in a Rat Femur Fracture Model." *Journal of Orthopaedic Research*, vol. 14, No. 5, pp. 802–809, 1996.

Young et al., "Effect of therapeutic ultrasound on the healing of full–thickness excised skin lesions." *Ultrasonics*, vol. 28, No. 3, pp. 175–180, 1990.

Young et al., "The Effect of Therapuetic Ultrasound On Angiogenesis." *Ultrasound in Medicine and Biology*, vol. 16, No. 3, pp. 261–269, 1990.

Chortkoff et al., "Pharmacokinetics Do Not Explain the Absence of an Anesthetic Effect of Perfluoropropane or Perfluoropentane." *Anesth. Analg.*, 79, pp. 234–237, 1994.

Sharma et al., "Emulsification Methods For Perfluorochemicals." *Drug Development And Industrial Pharmacy*, 14 (15–17), pp. 2371–2376 (1988).

Tilcock et al., "PEG–coated Lipid Vesicles with Encapsulated Technetium–99m as Blood Pool Agents for Nuclear Medicine." *2211b Nuclear Medicine and Biology*, 21, No. 2, pp. 165–170, 1994.

Tilcock et al., "$^{99m}$Tc–labeling of Lipid Vesicles Containing the Lipophilic Chelator PE–DTTA: Effect of Tin–to–chelate Ratio, Chelate Content and Surface Polymer on Labeling Efficiency and Biodistribution Behavior." *2211b Nuclear Medicine and Biology*, 21, No. 1, pp. 89–96, 1994.

Zarif et al., "Synergistic Stabilization of Perfluorocarbon–Pluronic F–68 Emulsion by Perfluoroalkylated Polyhydroxylated Surfactants." *JAOCS*, vol. 66, No. 10, pp. 1515–1523, 1989.

Ding et al., *Chung Kuo Yao Li Hsueh Pao,* Sep. 1989; 10(5):473–5 (Abstract only).

Ring et al., *Clinical Weekly*, 52, pp. 595–598 (1974) (German language only).

P.N.T. Wells, "Pulse–Echo Methods", *Biomedical Ultrasonics*, Academic Press, pp. 209–220 (1977).

Robinson, et al., F.J. Fry, ed., *Ultrasound: Its Applications In Medicine And Biology*, Elsevier Scientific Publishing Company, vol. 3, Chap. XI, pp. 593–596 (1978).

Silbernagl, Despopoulos, *Pocket Atlas of Physiology*, Georg Thieme Verlag, Stuttgart New York, pp. 156–157 (1983) (German language only).

H. Meessen, ed., *Microcirculation*, Springer–Verlag, Berlin Heidelberg, New York, p. 44 (1997) (German language only).

Kinsler, et al., *Fundamentals of Acoustics*, third ed., pp. 228–331 (1982).

Hynynen et al., "The Usefulness of a Contrast Agent and Gradient Recalled Acquisition in a Steady–State Imaging Sequence for Magnetic Resonance Imaging–Guided Noninvasive Ultrasound Surgery", *Investigative Radiology,* 1994, 29(10), 897–903.

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography,* 1998, 11(1), 36–46.

Regen et al., "Polymerized Phosphatidylcholine Vesicles. Synthesis and Characterization", *J. Am. Chem. Soc..* 1982, 104(3), 191–195.

Wei et al., "Quantification of Myocardial Blood Flow with Ultrasound–Induced Destruction of Microbubbles Administered as a Constant Venous Infusion", *Circulation,* 1998, 97, 473–483.

Nomura et al., "US Contrast Enhancement of Hepatic Tumor with Helium Gas Microbubbles: A Preliminary Report", *Jpn. J. Med. Ultrasonics,* 1991, 18(5), (Japanese with English language abstract).

Desir et al., "Assessment of regional myocardial perfusion with myocardial contrast echocardiography in a canine model of varying degrees of coronary stenosis", *Am. Heart J.*, vol. 127, No. 1, pp. 56–63 (Jan. 1994).

Sekins et al., "Lung Cancer Hyperthermia via Ultrasound and PFC Liquids", *Published in Proceedings of 5th International Symposium on Hyperthermic Oncology, Kyoto, Japan*, Aug. 29–Sep. 3, 1998, 3 pages.

Pietersen, "A New Warning System for Fires of Electrical Origin", *CERN European Organization for Nuclear Research, Health and Safety Division*, Mar., 1977, pp. 1–5.

Reexamination of U.S. patent No. 5,527,521, Reexam Control No. 90/004,719, 1999.

Reexamination of U.S. patent No. 5,547,656, Reexam Control No. 90/004,720, 2000.

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Feinstein, Steven B., "Myocardial Perfusion Imaging: Contrast Echocardiography Today and Tomorrow," *Journal of the American College of Cardiology*, 8(1):251–253 (1986).

Keller et al., "The Behavior of Sonicated Albumin Microbubbles Within the Microcirulation: A Basis for Their Use During Myocardial Contrast Echocardiography", *Circulation Res.*, vol. 65, No. 2, pp. 458–465 (Aug. 1989).

Lincoff et al., "Perfluoro–n–butane: A Gas for Maximum Duration Retinal Tamponade," *Arch Ophthalmology*, 101:460–462 (1983).

*Remington's Pharmaceutical Sciences*, John Hoover, managing ed., Mack Publishing Company, Easton, PA, pp. 295–298; 736; 1242–1244 (1975).

*Handbook of Pharmaceutical Excipients*, American Pharmaceutical Association, Washington, D.C. and The Pharmaceutical Society of Great Britain, London, England, pp. 181–183 (1986).

Miller et al., "Physiochemical Approaches to the Mode of Action of General Anesthetics," *J. Amer. Soc. Anesthesiologists*, 36(4):339–351 (1972).

"Properties and Applications of the 'Freon' Fluorocarbons" in DuPont Freon Technical Bulletin B–2 (E.I. DuPont de Nemours and Company, Wilmington, DE), pp. 1–11 (1964).

"'Freon' Fluorocarbons: Properties and Applications" in DuPont Technical Bulletin G–1 (E.I. DuPont de Nemours and Company, Wilmington, DE), pp. 1–10 (1987).

"Encyclopedia of Polymer Science and Engineering," John Wiley & Sons, New York, 1:164–169 (1985).

"Concise Encyclopedia of Polymer Science and Engineering," J. Kroschwitz, ed., John Wiley & Sons, New York, pp. 12–13 (1990).

Wheatley et al., "Contrast Agents for Diagnostic Ultrasound: Development and Evaluation of Polymer–Coated Microbubbles," *Biomaterials*, 11:713–717 (1990).

Lincoff et al., "Intravitreal Expansion of Perfluorocarbon Bubbles", *Arch. Ophthalmol.*, vol. 98, p. 1646, Sep. 1980.

Lincoff et al., "Intravitreal Longevity of Three Perfluorocarbon Gases", *Arch. Ophthalmol.*, vol. 98, pp. 1610–161, Sep. 1980.

Lincoff et al., "The Perfluorocarbon Gases in the Treatment of Retinal Detachment", *Ophthalmology*, vol. 90, No. 5, pp. 546–551, May 1983.

Gardner et al., "A Survey of Intraocular Gas Use in North America", *Arch. Ophthalmol.*, vol. 106, pp. 1188–1189, Sep. 1988.

Unger et al., "Liposomal MR Contrast Agents", *J. Liposome Research*,1994, 4(2), pp. 811–834.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Mattrey et al., *Gas Emulsions as Ultrasound Contrast Agents; Preliminary Results in Rabbits and Dogs, Investigative Radiology*, vol. 29, Jun. 1994 Supp. 2, pp. S139–S141.

Meltzer et al., *Transmission of Ultrasonic Contrast Through the Lungs, Ultrasound in Med. & Biol.*, vol. 7, No. 4, 377–384, 1981.

Chang et al., *Canadian J. of Physiology and Pharmacology,* vol. 44, pp. 115–128 and p. 513 (1966).

Chang, *Science*, vol. 146, pp. 524–525 (1964).

Deasy, *Microencapsulation and Related Drug Processes*, vol. 20, Chs. 9 and 10, pp. 195–240 (Marcel Dekker, Inc., NY) (1983).

Yeung et al., *J. Microencapsulation*, vol. 5, pp. 331–337 (1988).

Broomley, et al., "Microbubble contrast agents: a new era in ultrasound," *Clinical Review, BMJ*, May 19, 2001, XP008001399, 1222–1225.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., *Koordinatsionnaya Khimiya*, vol. 3, No. 4, pp. 524–527 (1977) (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of large unilamellar vesicles by a rapid extrusion procedure. Characterization of size distribution, trapped volume, and ability to maintain a membrane potential", *Biochimica et Biophysica Acta*, vol. 812, pp. 55–65 (1985).

Mayer et al., "Vesicles of Variable Size Produced by a Rapid Extrusion Procedure", *Biochimica et Biophysica Acta*, vol. 858, pp. 161–168 (1986).

Cheng et al., "The Production and Evaluation of Contrast--Carrying Liposomes Made with an Automatic High Pressure System", *Investigative Radiology*, vol. 22, No. 1, pp. 47–55 (1987).

Jain, et al., "Facilitated Transport", *Introduction to Biological Membranes*, Ch. 9, pp. 192–231 (J. Wiley and Sons, N.Y. 1980).

Sigel, H., ed., *Metal Ions in Biological Systems: Antibiotics and Their Complexes*, vol. 19 (Marcel Dekker, N.Y. 1985).

Nayar et al., "Generation of Large Unilamellar Vesticles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor Imaging and Hepatosplenography: Preliminary Clinical Results", *Radiology*, vol. 163, No. 2, pp. 339–343 (1987).

Mattrey et al., "Perfluoroctylbromide: A Liver/Spleen–Specific and Tumor–Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography. I. In Vitro Development and Quantitative Analysis of Echo Contrast Agents", *JACC*, vol. 3, No. 1 pp. 14–20 (1984).

Ten Cate et al., "Two–Dimensional Contrast Echocardiography. II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, No. 1, pp. 81–85 (1989).

Deamer et al., "Permeability of Lipid Bilayers to Water and Ionic Solutes", *Chemistry and Physics of Lipids*, vol. 40, pp. 167–188 (1986).

Gutknecht et al., "Diffusion of carbon dioxide through lipid bilayer membranes. Effects of carbonic anhydrase, bicarbonate, and unstirred layers", *Chemical Abstracts*, vol. 87, 34772q, p. 136 (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anaesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DPTA: Preparation and Characterization of Relaxivity", *Radiology*, vol. 171, No. 1, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman, "Physiochemical Properties of Phospholipids and Lipid–Water Systems", *Liposome Technology*, Gregoriadis, G., ed., Chapter 1, vol. 1, pp. 1–18 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Fukuda et al., "Polymer–Encased Vesicles Derived from Dioctadecyldimethylammonium Methacrylate", *J. Am. Chem. Soc.*, vol. 108, pp. 2321–2327 (1986).

Regen, "Polymerized Vesicles", *J. Am. Chem. Soc.*, vol. 102, pp. 6638–6640 (1980).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 22(2), pp. 141–147 (1987) (abstract).

Crowe et al., "Preservation of Freeze–Dried Liposomes by Trehalose", *Archives of Biochemistry and Biophysics*, vol. 242, pp. 240–247 (1985).

Crowe et al., "Preservation of Structural and Functional Activity in Lyophilized Sarcoplasmic Reticulum", *Archives of Biochemistry and Biophysics*, vol. 220, pp. 477–484 (1983).

Dorland's Illustrated Medical Dictionary, p. 946, 27th ed (W.B. Saunders Company, Philadelphia 1988).

*Liposome Technology*, Gregoriadis, G., ed., vol. I, pp. 1–18, 30–35, 51–65 and 79–107 (CRC Press Inc., Boca Raton, FL, (1984).

Madden et al., "The accumulation of drugs within large unilamellar vesicles exhibiting a proton gradient: a survey", *Chemistry and Physics of Lipids*, vol. 53, pp. 37–46 (1990).

Sinkula et al., "Rationale for Design of Biologially Reversible Drug Derivatives: Prodrugs", *J. Pharm. Sci.*, vol. 64, No. 2, pp. 181–210 (1975).

Shiina et al., "Hyperthermia by Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, vol. 249, pp. 2512–2521 (1974).

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for preparation of liposomes with large internal aqueous space...", *Proc. Natl. Acad. Sci.*, vol. 75, No. 9, pp. 4194–4198 (1978).

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., "Ultrasound Power and Intensitites Produced By Diagnostic Ultrasound Equipment", *Ultrasound in Med. & Biol.*, vol. 3, pp. 341–350 (1978).

Kost et al., *Polymers in Medicine II: Biomedical and Pharmaceutical Applications*, "Ultrasonic Modulated Drug Delivery Systems", Chiellini et al., eds., (Plenum Press, New York and London), pp. 387–396 (1985).

deGier et al., "Relations Between Liposomes and Biomembranes", *Annals of New York Academy of Sciences*, vol. 308, pp. 85–99 (1978).

Felgner et al., "Lipofection: A highly efficient, lipid–mediated DNA–transfection procedure", *Proc. Natl. Acad. Sci.*, vol. 84, pp. 7413–7417 (1987).

Gabizon et al., "Liposome formulations with prolonged circulation time in blood and enhanced uptake by tumors", *Proc. Natl. Acad. Sci.*, vol. 85, pp. 6949–6953 (1988).

Garelli, et al., "Incorporation of new amphiphilic perfluoroalkylated bipyridine platinum and palladium complexes into liposomes: stability and..." *Biochimica et Biophysica Acta*, vol. 1127, pp. 41–48 (1992).

Kawai et al., "New Procedure for DNA Transfection with Polycation and Dimethyl Sulfoxide", *Molecular and Cellular Biology*, vol. 4, No. 6, pp. 1172–1174 (1984).

Kuo et al., "Metallocene Antitumor Agents. Solution and Solid–State Molybdenocene Coordination...", *J. Am. Chem. Soc.*, vol. 113, No. 24, pp. 9027–9045 (1991).

MacDonald, *Mammalian Cell Biotechnology: A Practical Approach*, M. Butler, ed., (Oxford University Press, New York), Chapter 4, pp. 57–70 (1991).

Mathiowitz et al., "Photochemical Rupture of Microcapsules: A Model System", *Journal of Applied Polymer Science*, vol. 26, pp. 809–822 (1981).

May et al., "Cationic Liposomes Enable Bovine Herpesvirus Type 2 DNA to Infect Cells", *Acta virol.*, 1991, 35:107.

Poznansky et al., "Biological Approaches to the Controlled Delivery of Drugs: A Critical Review", *Pharmacol. Rev.*, vol. 36, No. 4, pp. 277–336 (1984).

Sato et al., "Recent Aspects In The Use Of Liposomes In Biotechnology And Medicine", *Prog. Lipid Res.*, vol. 31, No. 4, pp. 345–372 (1992).

Simons et al., "Antisense c–myb oligonucleotides inhibit intimal arterial smooth muscle cell accumulation in vivo", *Nature*, vol. 359, pp. 67–70 (1992).

Thompson, "At Age 2, Gene Therapy Enters a Growth Phase", *Science*, vol. 258, pp. 744–746 (1992).

Trubetskoy et al., "Cationic liposomes enhance targeted delivery and expression of exogenous DNA....", *Biochimica et Biophysica Acta*, vol. 1131, pp. 311–313 (1992).

Umemura et al., "Studies on Sonodynamic Cancer Therapy", *IEEE*, O–7803–0785, pp. 354–355 (1992).

Williams, "Human Gene Therapy: Searching for Better Vectors", ASM News [American Society for Microbiology] vol. 58, pp. 67–69 (1992).

Woodle et al., "Versatility in lipid compositions showing prolonged circulation...", *Biochimica et Biophysica Acta* 1992, 1105:193–200.

Zhou et al., "Targeted delivery of DNA by liposomes and polymers", *J. of Controlled Release*, vol. 19, pp. 269–274 (1992).

Mathiowitz et al., "Polyanhydride Microspheres as Drug Carriers. II. Microencapsulation by Solvent Removal", *Journal of Applied Polymer Science*, vol. 35, pp. 755–774 (1988).

Sankaram et al., "Cholesterol–Induced Fluid–Phase Immiscibility in Membranes", *Pro. Natl. Acad. Sci.*, vol. 88, pp. 8686–8690 (1991).

*Scientific Apparatus Catalog* 92/93 (VWR Scientific, 1991), "Syringes", pp.1511–1513; "Filtration, Syringe Filters", pp. 766–768; "Filtration, Membranes", pp. 750–753; "Filtration, Filter Holders", p. 744.

Gramiak et al., "Detection of Intracardiac Blood Flow by Pulsed Echo–Ranging", *Radiology*, vol. 100, pp. 415–418 (1971).

Feigenbaum et al., *Circulation*, "Indentification of Ultrasound Echoes from the Left Ventricle by Use of Intracardiac Injections of Indocyanine Green", vol. XL1, pp. 615–621 (Apr., 1970).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, 1991 Napa, California Meeting of the Society for Magnetic Resonance in Medicine.

Ter–Pogossian, "Physical Principles and Instrumentation", *Computed Body Tomography*, Lee, et al., eds., Raven Press, New York, Chapter 1, pp. 1–7 (1988).

Aronberg, "Techniques", *Computed Body Tomography*, Lee, et al., eds., Raven Press, New York, Chapter 2, pp. 9–36 (1988).

Lindner et al., "Myocardial Perfusion Characteristics and Hemodynamic Profile of MRX–115, a Venous Echocardiographic Contrast Agent, During Acute Myocardial Infarction," *J. Am. Soc. of Echocardiography*, vol. 11, No. 1, pp. 36–46 (Jan. 1998).

Miller, *Ultrasonics* (Sep. 1981), "Ultrasonic detection of resonant cavitation bubbles in a flow tube by their second-harmonic emissions," pp. 217–224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Chang, "Semipermeable Aqueous Microcapsules", *Canadian J. Of Phys. And Pharm.*, 1966, vol. 44, pp. 115–128 (1978).

Chang, "Semipermeable Microcapsules", *Science*, 1964, 146, 524–525.

Deasy, Microencapsulation and Related Drug Processes, vol. 20, Chs. 9 and 10, pp. 195–239 (1983) (Marcel Dekker, Inc., NY).

Yeung et al., "Preparation of Microencapsulated Liposomes", *J. Microencapsulation*, 1988, 5, 331–337.

Swanson et al., "Enhancement Agents for Ultrasound: Fundamentals", *Pharmaceuticals In Medical Imaging*, Chapter 22, pp. 682–687 (1990).

Barnhart et al., "Characteristics of ALBUNEX™: Air–Filled Microspheres for Echocardiography Contrast Enhancement," *Investigative Radiology*, 25:S162–164 (Sep. 1990).

Levene et al., "Characterization of ALBUNEX™," *J. Acoust. Soc. Am.*, 87 (Suppl. 1):569–70 (Spring 1990).

Porter, et al., "Multifold Sonicated Dilutions of Albumin with Fifty Percent Dextrose Improve Left Ventricular Contrast Videointensity After Intravenous Injection in Human Beings", *Journal of the American Society of Echocardiography*, vol. 7, No. 5, pp. 465–471, Sep.–Oct. 1994.

Porter, et al., "Visually Discernible Myocardial Echocardiographic Contrast After Intravenous Injection of Sonicated Dextrose Albumin Microbubbles Containing High Molecular Weight, Less Soluble Gases", *Journal of the American College of Cardiology*, vol. 25, No. 2, pp. 509–515, Feb. 1995.

Srinivasan, et al., "Characterization of Binding Sites, Extent of Binding, and Drug Interactions of Oligonucleotides with albumin", *Antisense Research and Development*, vol. 5, pp. 131–139, 1995.

Xie et al., "Acute Myocardial Ischemia and Reperfusion can be Visually Identified Non–invasively with Intravenous Perfluoropropane–Enhanced sonicated Dextrose Albumin Ultrasound Contrast", *Circulation*, vol. 90, No. 4, Part 2, Abstract 2989, Oct. 1994.

Broomley, et al., "Microbubble contrast agents : a new era in ultrasound,"*Clinical Review, BMJ*, May 19, 2001, XP008001399, 1222–1225.

\* cited by examiner

LOW DENSITY MICROSPHERES AND THEIR USE AS CONTRAST AGENTS FOR COMPUTED TOMOGRAPHY AND IN OTHER APPLICATIONS

This is a continuation of U.S. application Ser. No. 08/594,269, filed Jan. 30, 1996, now abandoned which is a divisional of U.S. patent application Ser. No. 08/456,738, filed Jun. 1, 1995, now U.S. Pat. No. 5,527,521, which is a divisional of U.S. patent application Ser. No. 08/449,090, filed May 24, 1995, now U.S. Pat. No. 5,547,656, which is a divisional of U.S. patent application Ser. No. 08/116,982, filed Sep. 7, 1993, now U.S. Pat. No. 5,456,900, which is a divisional of U.S. patent application Ser. No. 07/980.594, filed Jan. 19, 1993, now U.S. Pat. No. 5,281,408, which is a divisional of U.S. patent application Ser. No. 07/680,984, filed Apr. 5, 1991, now U.S. Pat. No. 5,205,290.

BACKGROUND OF THE INVENTION

Computed tomography (CT) is a widespread diagnostic imaging method which measures, in its imaging process, the radiodensity (electron density) of matter. This radiodensity is depicted using CT in terms of Hounsefield Units (HU). Hounsefield Units, named after the inventor of the first CT scanner, reflect the relative absorption of CT X-rays by matter, the absorption being directly proportional to the electron density of that matter. Water, for example, has a value of 0 HU, air a value of −1000 HU, and dense cortical bone a value of +1000 HU. Because of the similarity in density of various tissues in the body, however, contrast agents have been sought to change the relative density of different tissues, and improve the overall diagnostic efficacy of this imaging method.

In the search for contrast agents for CT, researchers have generally sought to develop agents that will increase electron density in certain areas of a region of the body (positive contrast agents). Barium and iodine compounds, for example, have been developed for this purpose. For the gastrointestinal tract, barium sulfate is used extensively to increase the radiodensity of the bowel lumen on CT scans. Iodinated water soluble contrast media are also used to increase density within the gastro-intestinal tract, but are not used as commonly as the barium compounds, primarily because the iodine preparations are more expensive than barium and prove less effective in increasing radiodensity within this region of the body.

Despite their widespread use, however, barium and iodine compounds are suboptimally effective as gastro-intestinal contrast agents for CT. For example, if the concentration is too low, there is little contrast. Conversely, if the concentration is too high, then these radiodense contrast agents cause beam hardening artifacts which are seen as streaks on the CT images. It is also difficult to visualize the bowel mucosa with either the barium or iodine contrast agents.

In an attempt to improve upon the efficacy of contrast agents for the gastrointestinal tract, lipid emulsions that are capable of decreasing electron density (negative contrast agents) have been developed. Because lipids have a lower electron density than water, lipids provide a negative density on CT (a negative HU value). While these lipid emulsions appear to be more effective than the barium and iodine agents at improving visualization of the mucosa of the bowel, these contrast agents have limitations. First, there is a limitation to the concentration of lipid which a patient can tolerably drink, which puts a limit on the change in density (or HU) which. the lipid based CT contrast agent can provide. Lipid emulsions are also frequently expensive. Furthermore, these lipid formulations are generally perishable, which provides for packaging and storage problems.

New and/or better contrast agents for computed tomography imaging are needed. The present invention is directed toward this important end.

SUMMARY OF THE INVENTION

The present invention is directed to computed tomography imaging, and more particularly to the use of a contrast medium comprising a substantially homogeneous aqueous suspension of low density microspheres to image the gastrointestinal region and other body cavities of a patient. In one embodiment, the low density microspheres are gas-filled.

Specifically, the present invention pertains to methods of providing an image of the gastrointestinal region or other body cavities of a patient comprising (i) administering to the patient the aforementioned contrast medium, and (ii) scanning the patient using computed tomography imaging to obtain visible images of the gastrointestinal region or other body cavities.

The present invention is further directed to methods for diagnosing the presence of diseased tissue in the gastrointestinal region or other body cavities of a patient comprising (i) administering to the patient the aforementioned contrast medium, and (ii) scanning the patient using computed tomography imaging to obtain visible images of any diseased tissue in the patient.

The present invention also provides diagnostic kits for computed tomography imaging of the gastro-intestinal region or other body cavities which include the subject contrast medium.

DETAILED DESCRIPTION OF THE INVENTION

A wide variety of different low density microspheres may be utilized in the present invention. Preferably, the microspheres (which are small spheres having a central void or cavity), are composed of biocompatible synthetic polymers or copolymers prepared from monomers such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, $\epsilon$-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, 2-methacryloyloxy-trimethylammonium chloride, and polyvinylidene, as well polyfunctional crosslinking monomers such as N,N'-methylenebisacrylamide, ethylene glycol dimethacrylates, 2,2'-(p-phenylenedioxy)-diethyl dimethacrylate, divinylbenzene, triallylamine and methylenebis-(4-phenyl-isocyanate), including combinations thereof. Preferable polymers include polyacrylic acid, polyethyleneimine, polymethacrylic acid, polymethylmethacrylate, polysiloxane, polydimethylsiloxane, polylactic acid, poly($\epsilon$-caprolactone), epoxy resin, poly(ethylene oxide), poly(ethylene glycol), and polyamide (nylon). Preferable copolymers include the following: polyvinylidene-polyacrylonitrile, polyvinylidene-polyacrylonitrile-polymethylmethacrylate, and polystyrene-polyacrylonitrile. A most preferred copolymer is polyvinylidene-polyacrylonitrile. The term biocompatible, as used herein in conjunction with the terms monomer or polymer, is employed in its conventional sense, that is, to denote polymers that do not substantially interact with the tissues, fluids and other components of the body in a adverse fashion in the particular application of interest, such as the aforementioned monomers and polymers. Other suitable biocompatible monomers and polymers will be readily apparent to those skilled in the art, once armed with the present disclosure.

The microspheres of the present invention are low density. By low density, it is meant that the microspheres of the invention have an internal void (cavity) volume which is at least about 75% of the total volume of the microsphere. Preferably, the microspheres have a void volume of at least about 80%, more preferably at least about 85%, even more preferably at least about 90%, of the total volume of the microspheres.

The microspheres may be of varying size, provided they are low density. Suitable size microspheres include those ranging from between about 1 and about 1000 microns in outside diameter, preferably between about 5 and about 70 microns in outside diameter. Most preferably, the microspheres are about 50 microns in outside diameter.

The microspheres of the invention may be prepared by various processes, as will be readily apparent to those skilled in the art, once armed with the present disclosure, such as by interfacial polymerization, phase separation and coacervation, multiorifice centrifugal preparation, and solvent evaporation. Suitable procedures which may be employed or modified in accordance with the present disclosure to prepare microspheres within the scope of the invention include those procedures disclosed in Garner et al., U.S. Pat. No. 4,179,546, Garner, U.S. Pat. No. 3,945,956, Cohrs et al., U.S. Pat. No. 4,108,806, Japan Kokai Tokkyo Koho 62 286534, British Patent No. 1,044,680, Kenaga et al., U.S. Pat. No. 3,293,114, Morehouse et al., U.S. Pat. No. 3,401,475, Walters, U.S. Pat. No. 3,479,811, Walters et al., U.S. Pat. No. 3,488,714, Morehouse et al., U.S. Pat. No. 3,615,972, Baker et al., U.S. Pat. No. 4,549,892, Sands et al., U.S. Pat. No. 4,540,629, Sands et al., U.S. Pat. No. 4,421,562, Sands, U.S. Pat. No. 4,420,442, Mathiowitz et al., U.S. Pat. No. 4,898,734, Lencki et al., U.S. Pat. No. 4,822,534, Herbig et al., U.S. Pat. No. 3,732,172, Himmel et al., U.S. Pat. No. 3,594,326, Sommerville et al., U.S. Pat. No. 3,015,128, Deasy, *Microencapsulation and Related Drug Processes,* Vol. 20, Chs. 9 and 10, pp. 195–240 (Marcel Dekker, Inc., N.Y., 1984), Chang et al., *Canadian J. of Physiology and Pharmacology,* Vol 44, pp. 115–129 (1966), and Chang, *Science,* Vol. 146, pp. 524–525 (1964), the disclosures of each of which are incorporated herein by reference in their entirety.

In accordance with the preferable synthesis protocol, the microspheres are prepared using a heat expansion process such as is described in Garner et al., U.S. Pat. No. 4,179,546, Garner, U.S. Pat. No. 3,945,956, Cohrs et al., U.S. Pat. No. 4,108,806, British Patent No. 1,044,680, and Japan Kokai Tokkyo Koho 62 286534. In general terms, the heat expansion process is carried out by preparing microspheres of an expandable polymer or copolymer which contain in their void (cavity) a volatile liquid. The microsphere is then heated, plasticising the microsphere and volatilizing the gas, causing the microsphere to expand to up to about several times its original size. When the heat is removed, the thermoplastic polymer retains at least some of its expanded shape. Microspheres produced by this process tend to be of particularly low density, and are thus preferred. The foregoing described process is well known in the art, and is referred to herein as the heat expansion process for preparing low density microspheres.

Polymers useful in the heat expansion process will be readily apparent to those skilled in the art and include thermoplastic polymers or copolymers, including polymers or copolymers of many of the monomers described above. Preferable of the polymers and copolymers described above include the following copolymers: polyvinylidene-polyacrylonitrile, polyvinylidene-polyacrylonitrile-polymethylmethacrylate, and polystyrene-polyacrylonitrile. A most preferred copolymer is polyvinylidene-polyacrylonitrile.

Volatile liquids useful in the heat expansion process will also be well known to those skilled in the art and include: aliphatic hydrocarbons such as ethane, ethylene, propane, propene, butane, isobutane, neopentane, acetylene, hexane, heptane; chlorofluorocarbons such as $CCl_3F$, $CCl_2F_3$, $CClF_3$, $CClF_2-CCl_2F_2$,

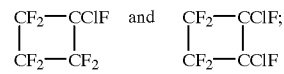

tetraalkyl silanes such as tetramethyl silane, trimethylethyl silane, trimethylisopropyl silane, and trimethyl n-propyl silane; as well as perfluorocarbons such as those having between 1 and about 9 carbon atoms and between about 4 and about 20 fluorine atoms, especially $C_4F_{10}$. In general, it is important that the volatile liquid not be a solvent for the microsphere polymer or copolymer. The volatile liquid should also have a boiling point that is below the softening point of the microsphere polymer or co-polymer. Boiling points of various volatile liquids and softening points of various polymers and copolymers will be readily ascertainable to one skilled in the art, and suitable combinations of polymers or copolymers and volatile liquids will be easily apparent to the skilled artisan. By way of guidance, and as one skilled in the art would recognize, generally as the length of the carbon chain of the volatile liquid increases, the boiling point of that liquid increases. Also, by mildly preheating the microspheres in water in the presence of hydrogen peroxide prior to definitive heating and expansion may pre-soften the microsphere to allow expansion to occur more readily.

For example, to produce microspheres of the present invention, vinylidene and acrylonitrile may be copolymerized in a medium of isobutane liquid using one or more of the foregoing modified or unmodified literature procedures, such that isobutane becomes entrapped within the microspheres. When such microspheres are then heated to between about 80° C. and about 120° C., the isobutane gas expands, which in turn expands the microspheres. After heat is removed, the expanded polyvinylidene and acrylo-nitrile copolymer microspheres remain substantially fixed in their expanded position. The resulting low density microspheres are extremely stable both dry and suspended in an aqueous media. Isobutane is utilized merely as an illustrative liquid, with the understanding that other liquids which undergo liquid/gas transitions at temperatures useful for the synthesis of these microspheres and formation of the very low density microspheres upon heating can be substituted for isobutane. Similarly, monomers other than vinylidene and acrylonitrile may be employed in preparing the microsphere.

Most preferably, the low density microspheres employed are those commercially available from Expancel, Nobel Industries, Sundsvall, Sweden, such as the EXPANCEL 551 DE™ microspheres. The EXPANCEL 551 DE™ microspheres are composed of a copolymer of vinylidene and acrylo-nitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

In one embodiment, the microspheres of the present invention are gas-filled. By gas-filled, it is meant that at least part of the void volume inside the microspheres is occupied by the gas. Preferably, substantially all of the void volume inside the microspheres is occupied by the gas. The gas may be any type of gas, such as, for example, carbon dioxide, oxygen, nitrogen, xenon, argon, neon, helium and air. Preferably, the gas is carbon dioxide, oxygen, nitrogen, xenon, argon, neon and helium. Most preferably, the gas is inert, that is, a gas that is substantially resistant to chemical or physical action. The gas-filled low density microspheres may be synthesized under pressure such that gases are solubilized in the liquid employed in microsphere synthesis. When the pressure is removed, the gas comes out of solution to fill the microsphere void. Such microspheres can further be subjected to a heat expansion process, as described above.

For example, to produce the gas-filled microspheres of the invention, one may copolymerize vinylidene and acrylonitrile using one or more of the foregoing procedures, such as phase separation/coacervation techniques in a pressurized and/or low temperature environment (e.g., at about 300 psi, and/or at about 0° C.) with a high concentration of dissolved gas (e.g., dissolved nitrogen) in solution, to form a large microsphere containing the dissolved gas. When the pressure is removed and/or the temperature raised, the gas bubbles come out of solution, forming gas filled microspheres. Such microspheres can further be subjected to a heat expansion process, as described above.

It is preferable that the microspheres be relatively stable in the gastrointestinal tract or other body cavities during the length of time necessary for completing an imaging examination. Low density microspheres prepared from the aforementioned monomer and polymer compositions will provide such stable microspheres.

In order for these microspheres to serve as effective CT contrast agents, it is necessary for the microspheres to be mixed in solution in a substantially homogeneous suspension. This can be accomplished by using thickening and suspending agents. A wide variety of thickening and suspending agents may be used to a prepare the substantially homogeneous suspensions of the microspheres. Suitable thickening and suspending agents, for example, include any and all biocompatible agents known in the art to act as thickening and suspending agents. Particularly useful are the natural thickening and suspending agents alginates, xanthan gum, guar, pectin, tragacanth, bassorin, karaya, gum arabic, casein, gelatin, cellulose, sodium carboxymethylcellulose, methylcellulose, methylhydroxycellulose, bentonite, colloidal silicic acid, and carrageenin, and the synthetic thickening and suspending agents polyethylene glycol, polypropylene glycol, and polyvinylpyrrolidone. As those skilled in the art would recognize, once armed with the present disclosure, the suspending agents may be formulated, if desired, to be either less dense than water or of neutral density, so as to not subtract from the density lowering capabilities of the microspheres. For example, a cellulose suspension may have a somewhat lower density than water, e.g., a 2 weight % cellulose solution with 0.25 weight % xanthan gum has a density of 0.95. The thickening and suspending agents may be employed in varying amounts, as those skilled in the art would recognize, but preferably are employed in amounts of about 0.25 to about 10 weight % preferably about 0.5 to about 5 weight % of the contrast medium.

The substantially homogeneous, aqueous suspension of low density microspheres of the invention are useful as CT contrast agents. These agents are capable of producing negative contrast in the gastrointestinal tract or in other body cavities, providing effective contrast enhancement and improved visualization in these areas of the body. Specifically, the present invention is directed to a method of providing an image of or detecting diseased tissue in the gastrointestinal region and other body cavities of a patient, the method comprising administering to the patient a contrast medium comprising a substantially homogeneous aqueous solution of low density microspheres, and scanning the patient using computed tomography imaging to obtain visible images of the gastrointestinal region or other body cavities or of diseased tissue in these areas of the body.

The phrase gastrointestinal region or gastrointestinal tract, as used herein, includes the region of a patient defined by the esophagus, stomach, small and large intestines, and rectum. The phrase other body cavities, as used herein, includes any region of the patient, other than the gastrointestinal region, having an open passage, either directly or indirectly, to the external environment, such regions including the sinus tracts, the fallopian tubes, the bladder, etc. The patient can be any type of mammal, but most preferably is a human.

As one skilled in the art would recognize, administration of the contrast medium to the patient may be carried out in various fashions, such as orally, rectally, or by injection. When the region to be scanned is the gastrointestinal region, administration of the contrast medium of the invention is preferably carried out orally or rectally. When other body cavities such as the fallopian tubes or sinus tracts are to be scanned, administration is preferably by injection. As would also be recognized by one skilled in the art, wide variations in the amounts of the gas filled microspheres can be employed in the methods and kits of the invention, with the precise amounts varying depending upon such factors as the mode of administration (e.g., oral, rectal, by injection), and the specific body cavity and portion thereof for which an image is sought (e.g., the stomach of the gastrointestinal tract). Typically, dosage is initiated at lower levels and increased until the desired contrast enhancement is achieved.

For CT imaging, it is generally desirable to decrease the density of the lumen of the gastrointestinal tract or other body cavities to at least about −30 HU, the maximum decrease being limited by the practical amount of the microspheres which may be suspended in the aqueous media and ingested by the patient. In general, a decrease in HU to between about −30 HU and about −150 HU is sufficient to mark the inside of the bowel or other body cavity. By way of general guidance, and as a rough rule of thumb, to decrease the density of the microsphere aqueous suspension to about −150 HU, the microspheres must occupy about 15% of the total volume of the aqueous suspension. To achieve a density of about −50 HU, the microspheres must occupy about 5% of the total volume of the solution. The volume of contrast agent administered to the patient is typically between about 50 to about 1000 cc. Using the EXPANCEL 551 DE™ microspheres as a model, it has been found that about 0.6 grams of the dry 50 micron spheres in 100 cc of aqueous suspension is sufficient to decrease the density of the suspension to nearly −150 HU.

It should be noted that smaller microspheres are generally more stable in suspension, but usually have higher specific gravity than larger microspheres. Therefore, for CT, the size and particular microspheres, as well as the suspending media (thickening and suspending agents) should selected to minimize specific gravity, while maximizing the stability of the suspension.

The contrast medium utilized of the present invention may also be employed with other conventional additives suitable for use in the applications contemplated for the subject invention.

Where gastrointestinal applications are concerned, such additives include conventional biocompatible anti-gas agents, osmolality raising agents, gastrointestinal transit agents (the later agents serving to decrease the gastrointestinal transit time and increase the rate of gastrointestinal emptying) and, in some instances, gas-forming agents.

As used herein the term anti-gas agent is a compound that serves to minimize or decrease gas formation, dispersion and/or adsorption. A number of such agents are available, including antacids, antiflatulents, antifoaming agents, and surfactants. Such antacids and antiflatulents include, for example, activated charcoal, aluminum carbonate, aluminum hydroxide, aluminum phosphate, calcium carbonate, dihydroxyaluminum sodium carbonate, magaldrate magnesium oxide, magnesium trisilicate, simethicone, sodium carbonate, loperamide hydrochloride, diphenoxylate, hydrochloride with atropine sulfate, Kaopectatew (kaolin) and bismuth salts. Suitable antifoaming agents useful as anti-gas agents include simethicone, protected simethicone, siloxyalkylene polymers, siloxane glycol polymers, polyoxypropylene-polyoxyethylene copolymers, polyoxyalkylene amines and imines, branched polyamines, mixed oxyalkylated alcohols, finely divided silica either alone or mixed with dimethyl polysiloxane, sucroglycamides (celynols), polyoxylalkylated natural oils, halogenated silicon-containing cyclic acetals, lauryl sulfates, 2-lactylic acid esters of unicarboxylic acids, triglyceride oils. Particles of polyvinyl chloride or silica may also function as antifoaming agents in the subject invention. Suitable surfactants include perfluorocarbon surfactants, such as, for example, DuPont Zonyl™ perfluoroalkyl surfactants known as Zonyl™ RP or Zonyl™ NF, available from DuPont, Chemicals and Pigments Division, Jackson Laboratory, Deepwater, N.J. 08023. Of course, as those skilled in the art will recognize, any anti-gas agents employed must be suitable for use within the particular biological system of the patient in which it is to be used. The concentration of such anti-gas agents may vary widely, as desired, as will be readily apparent to those skilled in the art. Typically, however, such agents are employed in concentrations of between about 20 and about 2000 ppm, most preferably in concentrations between about 50 and about 1000 ppm.

Suitable osmolality raising agents include polyols and sugars, for example, mannitol, sorbitol, arabitol, xylitol, glucose, sucrose, fructose, dextrose, and saccharine, with mannitol and sorbitol being most preferred. The concentration of such osmolality raising agents may vary, as desired, however, generally a range of about 5 to about 70 g/l, preferably about 30 to about 50 g/l of the contrast medium. Such compounds may also serve as sweeteners for the ultimate formulation, if desired.

Gastrointestinal transit agents include algin, as well as many of the compounds listed above as thickening and suspending agents, with algin being most preferred. The amount of such agents will, of course, vary as those skilled in the art will recognize, but generally will be employed in an amount of between about 5 and about 40 mmol/l.

In some applications, it may be helpful to incorporate gas-forming agents into the contrast medium. Gas-forming agents include sodium bicarbonate, calcium carbonate, aminomalonate, and the like, which will form gas, for example, upon introduction into the gastro-intestinal tract. Such gas-forming agents will serve to distend the gastrointestinal tract and create a form of "double contrast" between the gas and the low density microspheres.

Kits useful for computed tomography imaging of the gastrointestinal region or other body cavities in accordance with the present invention comprise low density microspheres, and a thickening or suspending agent, in addition to conventional computed tomography imaging kit components. Such conventional computed tomography kit components will be readily apparent to those skilled in the art, once armed with the present disclosure.

Where imaging of the gastrointestinal region is contemplated, such computed tomography kit components may include, for example, anti-gas agents, osmolality raising agents, gastrointestinal transit agents and, in some instances, gas-forming agents.

The computed tomography imaging principles and techniques which are employed are conventional and are described, for example, in *Computed Body Tomography*, Lee, J. K. T., Sagel, S. S., and Stanley, R. J., eds., Ch. 1, pp. 1–7 (Raven Press, N.Y. 1933). Any of the various types of computed tomography imaging devices can be used in the practice of the invention, the particular type or model of the device not being critical to the method of the invention.

The present invention is further described in the following Examples. Examples 1–7 are prophetic examples based at least in part on the teachings of Garner, U.S. Pat. No. 3,945,956, and describe the preparation of microspheres by a heat expansion process. Examples 8–9 are actual examples that describe the preparation of contrast media of the invention. The following Examples are not to be construed as limiting the scope of the appended Claims.

EXAMPLES

Example 1

A vessel is filled with 50 parts by weight of deionized water and 6 parts by weight of a 25 percent by weight aqueous colloidal silica dispersion. A mixture of 0.3 parts by weight of a 10 weight percent solution of diethylamine-adipic acid copolymer is added to the above. A condensation reaction occurs creating a mixture having a viscosity of about 95 centipoise at a temperature of about 27° C. Potassium dichromate (0.05 parts by weight) is added to the aqueous phase as a water phase polymerization inhibitor. Sodium chloride (1 part by weight) is also present in the water phase; hydrochloric acid is used to adjust the pH of the aqueous phase to 4.0. Styrene (15 parts by weight), acrylonitrile (10 parts by weight), a mixture of diethylbenzene and divinylbenzene (0.21 parts by weight comprising a 55:45 percent mixture of each respectively), 6.25 parts by weight of isobutane and 0.07 parts by weight of secondary butyl peroxydicarbonate. The oil phase is added to the water phase with violent agitation created by a shearing blade rotating at 10,000 RPM employing a mixing blender. After the material has reacted for about 30 minutes, the mixture is poured into a citrate bottle and capped. The material is maintained at about 50° C. in the citrate bath for about 24 hours and agitated throughout this time. At the end of 24 hours, the reaction bottle is cooled and the material is removed, washed and dried. A portion of the microspheres are set aside and the remainder are heated in an air oven for a period of about 30 minutes at about 150° C. A sample of the dry unexpanded and dry expanded microspheres are then studied by a Coulter Counter. The dry unexpanded microspheres have a size of about 2 to 12 microns. About half of the microspheres exposed to the heating process show expansion.

Example 2

The procedures of Example 1 are substantially repeated with the exception that 1 part by weight of methanol is added to the reaction mixture. The dry unexpanded and dry heat expanded microspheres are then studied by Coulter Counter. The dry unexpanded microspheres measure about 8 to 10 microns in size. Essentially all the microspheres exposed to heat expand.

Example 3

The procedures of Example 2 are substantially repeated except that after synthesis of the microspheres, a slurry of the microspheres is added to an aqueous solution containing 35 weight percent hydrogen peroxide. This slurry is heated to a temperature of about 50° C. for about 3.5 hours and subsequently cooled and air-dried. A portion of the microspheres is then added to water and heated to a temperature of about 75° C. with vigorous stirring for about 30 seconds. Study with Coulter Counter shows that pretreatment with hydrogen peroxide enables a lower temperature and briefer period of heating to be used for definitive heating and expansion.

Example 4

The procedures of Example 1 are substantially repeated with the exception that 5 parts by weight of ethanol are included in the reaction mixture forming the microspheres. Coulter Counter shows that the dry unexpanded particles have diameters of about 24 to 28 microns. When heated, essentially all of the microspheres expand.

Example 5

The procedures of Example 1 are substantially repeated with the exception that in place of methanol, 1 part by weight of normal butanol is used. The diameter of the dry unexpanded microspheres is about 10 to 12 microns and on heating, essentially all of the microspheres expand.

Example 6

The procedures of Example 1 are substantially repeated with the exception that the volatile liquid isobutane is replaced with perfluorocarbon liquid ($C_4F_{10}$). The remainder of the process is similar. The resulting microspheres are filled with perfluorocarbon liquid rather than isobutane.

Example 7

The procedures of Example 1 are substantially repeated with the exception that the reaction is conducted in a pressurized vessel enabling pressurization with gas and simultaneous agitation (agitation accomplished with either sonication or shearing blades within the device). As the microspheres are formed within the device, the vessel is pressurized to about 300 psi with nitrogen gas. The vessel is then depressurized, allowing the gas to come out of solution. The microspheres are then subjected to heat as substantially described in Example 1.

Example 8

A suspension of 2% of 22 micron fiber length cellulose in 0.25% xanthan gum in water was prepared. Scans by CT showed a CT density of about −45 HU for the cellulose suspension. EXPANCEL 551 DE™ polyvinylidene-polyacrylonitrile microspheres, 50 microns in size, were then suspended in the aqueous cellulose suspension at a concentration of 0.4 grams of microspheres per 100 ml of cellulose suspension using vigorous shaking. The resulting suspension remained substantially homogeneous for about 10 minutes. The suspension was again shaken vigorously to render it substantially homogeneous and scanned immediately by CT. The resulting CT density as measured by the scanner was about −96 HU.

Example 9

A suspension of 1% algin was prepared. EXPANCEL 551 DE™ microspheres were added to the algin suspension in an amount of about 0.2 grams of microspheres per deciliter of algin suspension, using vigorous shaking, to form a substantially homogeneous suspension. The resulting suspension was found to have much greater stability than the cellulose/microsphere suspension of Example 1. The algin/microsphere suspension was then scanned by CT, with the density as measured by the scanner being about −40 HU.

Various modifications of the invention in addition to those shown and described herein will be apparent to those skilled in the art from the foregoing description. Such modifications are also intended to fall within the scope of the appended Claims.

What is claimed is:

1. A low density gas-filled microsphere having an internal void volume of at least about 75% of the total volume of the microsphere, wherein said gas comprises a perfluorocarbon.

2. A microsphere according to claim 1 wherein said microspheres comprise synthetic polymers or copolymers prepared from the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl methacrylate, vinyl pyridine, aminoethyl methacrylates, 2-methacryloyloxy-trimethylammonium chloride, N,N'-methylenebisacrylamide, ethylene glycol dimethacrylates, 2,2'-(p-phenylenedioxy)-diethyl dimethacrylate, divinylbenzene, triallylamine, and methylenebis-(4-phenyl-isocyanate).

3. A microsphere according to claim 2 wherein said microsphere comprise synthetic polymers or copolymers prepared from the group of monomers consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethylmethacrylate, vinyl pyridine, aminoethyl methacrylates, and 2-methacryloyloxy-trimethylammonium chloride.

4. A microsphere according to claim 1 wherein said microsphere comprise synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), polyamide, polyvinylidene-polyacrylonitrile, polyvinylidene-poly-acrylonitrile-polymethylmethacrylate, and polystyrene-polyacrylonitrile.

5. A microsphere according to claim 1 wherein said microsphere comprise a polyvinylidene-polyacrylonitrile copolymer.

6. A microsphere according to claim 1 wherein said microsphere comprises a polyoxypropylene-polyoxyethylene copolymer.

7. A microsphere according to claim 1 wherein said microsphere is prepared by a heat expansion process.

8. A microsphere according to claim 1 wherein said perfluorocarbon gas is selected from the group consisting of perfluorocarbons having between 1 and about 9 carbon atoms and between about 4 and about 20 fluorine atoms.

9. A microsphere according to claim 8 wherein said perfluorocarbon gas is selected from the group consisting of perfluorocarbons having less than about 4 carbon atoms and less than about 10 fluorine atoms.

10. A microsphere according to claim 8 wherein said perfluorocarbon gas is $C_4F_8$.

11. A microsphere according to claim 1 wherein said microsphere comprises a polymer.

12. A microsphere according to claim 11 wherein said polymer is prepared from a polyfunctional crosslinking monomer.

13. A microsphere according to claim 2 wherein said polymer comprises an acrylate.

14. A microsphere according to claim 2 wherein said polymer comprises a methacrylate.

15. A microsphere according to claim 2 wherein said polymer comprises a cyanoacrylate.

16. A microsphere according to claim 1 which has an outside diameter of from about 5 to about 70 microns.

* * * * *

UNITED STATES PATENT AND TRADEMARK OFFICE
CERTIFICATE OF CORRECTION

PATENT NO.  : 6,528,039 B2
DATED       : March 4, 2003
INVENTOR(S) : Evan C. Unger It is certified that error appears in the above-identified patent and that said Letters Patent is hereby corrected as shown below:

Title page,
Item [56], References Cited, U.S. PATENT DOCUMENTS,
"4,533,254" reference, please delete "8/1965" and insert -- 8/1985 -- therefor.
"3,535,500" reference, please delete "3,535,500" and insert -- 3,532,500 -- therefor.
"4,334,929" reference, please delete "4,334,929" and insert -- 4,344,929 -- therefor.
"7,866,096" reference, please delete "7,866,096" and insert -- 4,866,096 -- therefor.
"4,987,754" reference, please delete "4,987,754" and insert -- 4,987,154 -- therefor.
"5,193,183" reference, please delete "5,193,183" and insert -- 5,196,183 -- therefor.
"5,846,514" reference, please delete "5,846,514" and insert -- 5,845,517 -- therefor.
Please add references:
-- 4,303,736    12/1981     Torobin ......         428/403
   4,582,756    4/1986      Niinuma et al. ......  428/327
   4,229,360 B1 11/1991     Schneider et al. ......  270/403 --.
Please delete reference "4,229,360 B1   11/1991   Schneider et al. .....270/403".
FOREIGN PATENT DOCUMENTS,
"WOX 85/01161" reference, please delete "WOX 85/01161 6/1988" and insert
-- WO 85/01161 3/1985 -- therefor.
"WO 84/02909" reference, please delete "8/1994" and insert -- 8/1984 -- therefor.
OTHER PUBLICATIONS,
"Trevino, L., et al.," reference, please delete "60".
"Wang et al.," reference, please delete "Fractural" and insert -- Fracture -- therefor.
"Villanueva et al.," reference, please delete "Patters" and insert -- Patterns -- therefor.
"Keller et al.," reference, please delete "Microcirulation" and insert
-- Microcirculation --; and please delete "458-465" and insert -- 468-467 -- therefor.
"Lincoff et al.," reference, please delete "1610-161" and insert -- 1610-1611 -- therefor.
"Nayer et al.," reference, please delete "Vesticles" and insert -- Vesicles -- therefor.
"Sinkula et al.," reference, please delete "Biologially" and insert -- Biologically --
therefor.

Column 4,
Line 55, please delete "acrylo-nitrile" and insert -- acrylonitrile -- therefor.

Column 5,
Line 4, please delete "acrylo-nitrile" and insert -- acrylonitrile -- therefor.

Column 7,
Line 5, following "should" and before "selected", please insert -- be --.
Line 27, please delete "Kaopectatew" and insert -- Kaopectate[TM] -- therefor.

UNITED STATES PATENT AND TRADEMARK OFFICE
CERTIFICATE OF CORRECTION

PATENT NO. : 6,528,039 B2
DATED : March 4, 2003
INVENTOR(S) : Evan C. Unger

It is certified that error appears in the above-identified patent and that said Letters Patent is hereby corrected as shown below:

Column 10,
Line 33, please delete "microspheres comprise" and insert -- microsphere comprises -- therefor.
Line 53, please delete "comprise" and insert -- comprises -- therefor.

Column 11,
Lines 2 and 12, please delete "comprise" and insert -- comprises -- therefor.

Column 12,
Line 6, please delete "$C_4F_8$" and insert -- $C_4F_{10}$ -- therefor.

Signed and Sealed this

First Day of February, 2005

JON W. DUDAS
*Director of the United States Patent and Trademark Office*